United States Patent
Wasserman et al.

(10) Patent No.: US 11,642,514 B2
(45) Date of Patent: May 9, 2023

(54) OPTIMIZING POSITIONS OF ELECTRODES FOR APPLYING TUMOR TREATING FIELDS (TTFIELDS) BY ADDING A DIPOLE TO A 3D MODEL

(71) Applicant: Novocure GmbH, Root (CH)

(72) Inventors: Yoram Wasserman, Haifa (IL); Cornelia Wenger, Ericeira (PT); Pedro Michael Cavaleiro Miranda, Lisbon (PT); Zeev Bomzon, Kiryat Tivon (IL); Noa Urman, Pardes Hanna Carcur (IL); Eilon Kirson, Ramat Hasharon (IL); Yoram Palti, Haifa (IL)

(73) Assignee: Novocure GmbH, Root (CH)

( * ) Notice: Subject to any disclaimer, the term of this patent is extended or adjusted under 35 U.S.C. 154(b) by 268 days.

(21) Appl. No.: 17/190,979

(22) Filed: Mar. 3, 2021

(65) Prior Publication Data

US 2021/0187277 A1    Jun. 24, 2021

Related U.S. Application Data

(60) Continuation of application No. 16/222,042, filed on Dec. 17, 2018, now Pat. No. 11,013,909, which is a
(Continued)

(51) Int. Cl.
*A61B 5/05* (2021.01)
*A61B 5/053* (2021.01)
(Continued)

(52) U.S. Cl.
CPC .......... *A61N 1/0456* (2013.01); *A61B 5/0042* (2013.01); *A61B 5/05* (2013.01);
(Continued)

(58) Field of Classification Search
CPC ....... A61B 5/0042; A61B 5/053; A61B 5/055; A61N 1/0456; A61N 1/36002;
(Continued)

(56) References Cited

U.S. PATENT DOCUMENTS

| 5,568,816 A | 10/1996 | Gevins et al. |
| 6,868,289 B2 | 3/2005 | Palti |

(Continued)

FOREIGN PATENT DOCUMENTS

| CN | 101578119 A | 11/2009 |
| CN | 104063565 A | 9/2014 |

(Continued)

OTHER PUBLICATIONS

Li et al., "BrainK for Structural Image Processing: Creating Electrical Models of the Human Head," Computational Intelligence and Neuroscience, vol. 2016, Article ID 1349851, 2016.
(Continued)

*Primary Examiner* — Brian T Gedeon
(74) *Attorney, Agent, or Firm* — Potomac Law Group, PLLC

(57) ABSTRACT

When electrodes are used to impose an electric field in target tissue within an anatomic volume (e.g., to apply TTFields to treat a tumor), the position of the electrodes can be optimized by generating a 3D map of electrical conductivity or resistivity of the anatomic volume. A location of the target tissue within the anatomic volume is identified, and a dipole is added to the 3D map at a location that corresponds to the target tissue. positions for the electrodes that maximize a potential attributable to the dipole are determined based on the 3D map of electrical conductivity or resistivity and the location of the dipole.

9 Claims, 7 Drawing Sheets

Related U.S. Application Data division of application No. 15/336,660, filed on Oct. 27, 2016, now Pat. No. 10,188,851.

(60) Provisional application No. 62/294,372, filed on Feb. 12, 2016, provisional application No. 62/247,314, filed on Oct. 28, 2015.

(51) Int. Cl.

| | | |
|---|---|---|
| *A61B 5/055* | (2006.01) | |
| *A61B 5/24* | (2021.01) | |
| *A61B 5/316* | (2021.01) | |
| *A61B 5/00* | (2006.01) | |
| *A61N 1/40* | (2006.01) | |
| *G16H 50/50* | (2018.01) | |
| *A61N 1/04* | (2006.01) | |
| *A61N 1/36* | (2006.01) | |
| *G16Z 99/00* | (2019.01) | |
| *A61N 1/32* | (2006.01) | |

(52) U.S. Cl.
CPC .............. *A61B 5/053* (2013.01); *A61B 5/055* (2013.01); *A61B 5/24* (2021.01); *A61B 5/316* (2021.01); *A61B 5/4064* (2013.01); *A61N 1/0476* (2013.01); *A61N 1/32* (2013.01); *A61N 1/36002* (2017.08); *A61N 1/36025* (2013.01); *A61N 1/40* (2013.01); *G16H 50/50* (2018.01); *G16Z 99/00* (2019.02)

(58) Field of Classification Search
CPC .......... A61N 1/0476; A61N 1/08; A61N 1/32; A61N 1/36025; A61N 1/40; G16H 50/50
See application file for complete search history.

(56) References Cited

U.S. PATENT DOCUMENTS

| | | |
|---|---|---|
| 7,016,725 B2 | 3/2006 | Palti |
| 7,089,054 B2 | 8/2006 | Palti |
| 7,136,699 B2 | 11/2006 | Palti |
| 7,146,210 B2 | 12/2006 | Palti |
| 7,333,852 B2 | 2/2008 | Palti |
| 7,467,011 B2 | 12/2008 | Palti |
| 7,519,420 B2 | 4/2009 | Palti |
| 7,565,205 B2 | 7/2009 | Palti |
| 7,565,206 B2 | 7/2009 | Palti |
| 7,599,745 B2 | 10/2009 | Palti |
| 7,599,746 B2 | 10/2009 | Palti |
| 7,706,890 B2 | 4/2010 | Palti |
| 7,715,921 B2 | 5/2010 | Palti |
| 7,805,201 B2 | 9/2010 | Palti |
| 7,890,183 B2 | 2/2011 | Palti et al. |
| 7,912,540 B2 | 3/2011 | Palti |
| 7,917,227 B2 | 3/2011 | Palti |
| 8,019,414 B2 | 9/2011 | Palti |
| 8,027,738 B2 | 9/2011 | Palti |
| 8,170,684 B2 | 5/2012 | Palti |
| 8,175,698 B2 | 5/2012 | Palti et al. |
| 8,229,555 B2 | 7/2012 | Palti |
| 8,244,345 B2 | 8/2012 | Palti |
| 8,406,870 B2 | 3/2013 | Palti |
| 8,447,395 B2 | 5/2013 | Palti et al. |
| 8,447,396 B2 | 5/2013 | Palti et al. |
| 8,465,533 B2 | 6/2013 | Palti |
| 9,020,789 B2 | 4/2015 | Butson et al. |
| 9,307,925 B2 | 4/2016 | Russell et al. |
| 9,760,688 B2 | 9/2017 | McIntyre et al. |
| 10,188,851 B2 | 1/2019 | Wenger et al. |
| 10,441,776 B2 | 10/2019 | Kirson et al. |
| 10,779,875 B2 | 9/2020 | Palti et al. |
| 10,821,283 B2 | 11/2020 | Giladi et al. |
| 2006/0017749 A1 | 1/2006 | McIntyre et al. |
| 2006/0167499 A1 | 7/2006 | Palti |
| 2006/0282122 A1 | 12/2006 | Palti |
| 2007/0033660 A1 | 2/2007 | Palti |
| 2007/0043268 A1 | 2/2007 | Russell |
| 2007/0225766 A1 | 9/2007 | Palti |
| 2007/0239213 A1 | 10/2007 | Palti |
| 2009/0076366 A1 | 3/2009 | Palti |
| 2010/0113959 A1 | 5/2010 | Pascual-Leone et al. |
| 2011/0137229 A1 | 6/2011 | Palti et al. |
| 2011/0288400 A1 | 11/2011 | Russell et al. |
| 2012/0197243 A1 | 8/2012 | Sherman et al. |
| 2012/0265261 A1 | 10/2012 | Bikson et al. |
| 2012/0283726 A1 | 11/2012 | Palti |
| 2013/0178819 A1 | 7/2013 | Palti et al. |
| 2013/0178820 A1 | 7/2013 | Palti et al. |
| 2013/0184637 A1 | 7/2013 | Palti |
| 2013/0184674 A1 | 7/2013 | Palti |
| 2014/0330268 A1 | 11/2014 | Palti et al. |
| 2016/0081577 A1 | 3/2016 | Sridhar et al. |
| 2017/0120041 A1 | 5/2017 | Wenger et al. |
| 2017/0215939 A1 | 8/2017 | Palti et al. |
| 2017/0281934 A1 | 10/2017 | Giladi et al. |
| 2018/0001075 A1 | 1/2018 | Kirson et al. |
| 2018/0008708 A1 | 1/2018 | Giladi et al. |
| 2018/0050200 A1 | 2/2018 | Wasserman et al. |
| 2018/0160933 A1 | 6/2018 | Urman et al. |
| 2018/0202991 A1 | 7/2018 | Giladi et al. |
| 2019/0117956 A1 | 4/2019 | Wenger et al. |
| 2019/0117963 A1 | 4/2019 | Travers et al. |
| 2019/0307781 A1 | 10/2019 | Krex et al. |
| 2019/0308016 A1 | 10/2019 | Wenger et al. |
| 2020/0001069 A1 | 1/2020 | Kirson et al. |
| 2020/0009376 A1 | 1/2020 | Chang et al. |
| 2020/0009377 A1 | 1/2020 | Chang et al. |
| 2020/0016067 A1 | 1/2020 | Gotlib et al. |
| 2020/0023179 A1 | 1/2020 | Bomzon et al. |
| 2020/0061360 A1 | 2/2020 | Hagemann et al. |
| 2020/0061361 A1 | 2/2020 | Hagemann et al. |
| 2020/0069937 A1 | 3/2020 | Naveh et al. |
| 2020/0078582 A1 | 3/2020 | Alon et al. |
| 2020/0108031 A1 | 4/2020 | Borst et al. |
| 2020/0121728 A1 | 4/2020 | Wardak et al. |
| 2020/0129761 A1 | 4/2020 | Bomzon et al. |
| 2020/0146586 A1 | 5/2020 | Naveh et al. |
| 2020/0155835 A1 | 5/2020 | Wasserman et al. |
| 2020/0171297 A1 | 6/2020 | Kirson et al. |
| 2020/0179512 A1 | 6/2020 | Giladi et al. |
| 2020/0219261 A1 | 7/2020 | Shamir et al. |
| 2020/0254242 A1 | 8/2020 | Chang et al. |
| 2020/0269037 A1 | 8/2020 | Hagemann et al. |
| 2020/0269041 A1 | 8/2020 | Zeevi et al. |
| 2020/0269042 A1 | 8/2020 | Giladi et al. |
| 2020/0269043 A1 | 8/2020 | Wasserman et al. |
| 2020/0306531 A1 | 10/2020 | Tran et al. |
| 2020/0330755 A1 | 10/2020 | Wasserman et al. |

FOREIGN PATENT DOCUMENTS

| | | |
|---|---|---|
| CN | 104123416 A | 10/2014 |
| JP | H09173315 A | 7/1997 |
| WO | 2004030760 A2 | 4/2004 |
| WO | 2005069032 A1 | 7/2005 |
| WO | 2012052543 A1 | 4/2012 |

OTHER PUBLICATIONS

Basser, et al.; "MR Diffusion Tensor Spectroscopy and Imaging," Biophysical Journal, vol. 66, pp. 259-267 (Jan. 1994).

Bomzon, et al.; Modelling Tumor Treating Fields fo rthe Treatment of Lung-Based Tumors, Proceedings of Engineering in Medicine and Biology Society, 2015 37th Annual International Conference of the IEEE, Aug. 25-29, 2015.

Chaudhry, et al, "NovoTTFTM-100A System (Tumor Treating Fields) transducer array layout planning for glioblastoma: a NovoTALTM system user study," World J Surg Oncol, 13:316 (2015), published online: Nov. 11, 2015.

Dyrby, et al.; "Interpolation of diffusion weighted imaging datasets," Neuroimage, 103:202-213 (2014).

(56) References Cited

OTHER PUBLICATIONS

Fonkem and E.T. Wong, "NovoTTF-IO0A: a new treatment modality for recurrent glioblastoma," Expert Rev. Neurotherapeutics, 12(8): 895-899 (2012).

Gullmar, et el.; "Influence of Anisotropic Electrical Conductivity in White Matter Tissue on the EEG/MEG Forward and Inverse Solution—A High-Resolution Whole Head Simulation Study"; NeuroImage, Mar. 15, 2010, 51 (1):145-163.

Gutin, et al.; "Noninvasive Application of Alternating Electric Fields in Glioblastoma: A Fourth Cancer Treatment Modality.," Am. Soc. Clin. Oneal. Educ. Book, vol. 32, pp. 126-131, Jan. 2012.

International Search Report and Written Opinion issued in PCT Application No. PCT/IB2016/056495 dated Jan. 24, 2017.

Irfanoglu, et al.; "DR-BUDDI (Diffeomorphic Registration for Blip-Up blip-Down Diffusion Imaging) method for correcting echo planar imaging distortions," Neuroimage, 106:284-299 (Feb. 2015).

Jenkinson, et al., "FSL," NeuroImage, 62(2):782-790, Aug. 2012.

Joy, et al.; "Electrical conductivity imaging using MRI measurement of the magnetic field vector"; Proceedings of Engineering in Medicine and Biology Society, 2009, Annual International conference of the IEEE, Sep. 3-6, 2009, pp. 3158-3161.

Khan; "Treatment Planning I: Isodose Distributions," The Physics of Radiation Therapy, 5th Edition, Chapter 11, pp. 170-194, 2014.

Kim, et al., "Simultaneous Imaging of In-vivo Conductivity and Susceptibility," Magn. Reson. Med., 71 (3):1144-1150 (Mar. 2014).

Kirson et al.; "Alternating electric fields arrest cell proliferation in animal tumor models and human brain tumors" Proc. Natl. Acad. Sci. U.S.A., 104(24):10152-10157 (Jun. 2007).

Kirson et al.; "Disruption of cancer cell replication by alternating electric fields"; Cancer Research, 64(9): 3288-3295 (May 2004).

Lok, et al.; "Computed modeling of alternating electric fields therapy for recurrent glioblastoma," Cancer Medicine 2015, 4(11):1697-1699.

Miranda, et al.; "Predicting the electric field distribution in the brain for the treatment of glioblastoma," Phys Med Biol, 59(15):4137-4147 (Aug. 2014).

Mrugala, et al.; "Clinical practice experience with NovoTTF-IO0A™ system for glioblastoma: The Patient Registry Dataset (PRiDe).," Seminars in Oncology, 41(5) Supp. 6:S4-S13 (Oct. 2014).

Opitz et al., "How the brain tissue shapes the electric field induced by transcranial magnetic stimulation", NeuroImage (Jul. 1, 2011), vol. 58(3), pp. 849-859.

Pierpaoli, et al.; "TORTOISE: an integrated software package for processing of diffusion MRI data," ISMRM Joint Annual Meeting, May 1-7, 2010, 18(1):1597 (2010).

Pierpaoli, et al.; "Toward a Quantitative Assessment of Diffusion Anisotropy," Magn. Reson. Med., 36(6):893-906 (Dec. 1996).

Porz, et al., "Multi-modal glioblastoma segmentation: Man versus machine," PLoS One, 9(5) pp. 1-9 (May 2014).

Roth et al., "A theoretical calculation of the electric field induced in the cortex during magnetic stimulation", Electroencephalography and Clinical Neurophysiology/Evoked Potentials Section (Feb. 1, 1991), vol. 81(1), pp. 47-56.

Rullmann et al.; "EEG source analysis of epileptiform activity using a 1mm anisotropic hexahedra finite element head model"; Neuroimage, Jan. 15, 2009, 44(2):399-410.

Sanjuan, et al. "Automated identification of brain tumors from single MR images based on segmentation with refined patient-specific priors.," Front. Neurosci., vol. 7, article 241, pp. 1-12 (Dec. 2013).

Sekino, et al.; "Conductivity tensor imaging of the brain using diffusion-weighted magnetic resonance imaging", J Appl Phys, vol. 93, No. 10, pp. 6730-6732, 2003.

Shattuck et al., "BrainSuite: an automated cortical surface identification tool.," Med. Image Anal., 6(2):129-142 (Jun. 2002).

Simi, et al.; "Segmentation of Glioblastoma Multiforme from MR Images—A comprehensive review," Egypt. J. Radiol. Nucl. Med., 46:1105-1110 (2015); available online Aug. 21, 2015.

Smith, et al.; "Advances in Functional and Structural MR Image Analysis and Implementation as FSL," NeuroImage, 23(Supp. 1):S208-S219 (2004).

Soares, et al.; "A hitchhiker's guide to diffusion tensor imaging"; Frontiers in Neuroscience, Mar. 2013, vol. 7, Article 31, pp. 1-14.

Stupp, et al., "NovoTTF-100A versus physician's choice chemotherapy in recurrent glioblastoma: a randomised phase III trial of a novel treatment modality"; Eur. J. Cancer, 48(14):2192-2202 (Sep. 2012).

Stupp, et al.; "NT-40 Interim analysis of the EF-14 trial: A prospective, multi-center trial of NovoTTF-100A together with temozolomide compared to temozolomide alone in patients with newly diagnosed GBM"; Neuro-Oncology, 16:v1 (Nov. 2014).

Tuch, et al.; "Conductivity tensor mapping of the human brain using diffusion tensor MRI.," Proc. Natl. Acad. Sci. USA., 98(20):11697-11701 (Sep. 2001).

Turner, et al., "The effect of field strength on glioblastoma multiforme response in patients treated with the NovoTTF-IO0A system," World J Surg Oncology 2014, 12:162, pp. 1-5.

Wenger et al., "Improving Tumor Treating Fields Treatment Efficacy in Patients with Glioblastoma Using Personalized Array Layouts," International Journal of Radiation Oncology Biology Physics, vol. 94, No. 5, pp. 1137-1143, 2016.

Wenger, "Alternating electric fields (TTFields) for treating glioblastomas: a modeling study on efficacy," Neuro-Oncolgoy, Oct. 2014.

Wenger, et al., "Investigating the mechanisms of action of tumor treating fields: a computational modeling study," Neuro-Oncolgy, 16(Supp 5):v216, (Nov. 2014).

Wenger, et al.; "Electric fields for the treatment of glioblastomas: a modeling study," Neuro-Oncolgy, vol. 15, No. suppl3, p. TM-028, 2013.

Wenger, et al.; "The Electric Field Distribution in the Brain During TTFields Therapy and Its Dependence on Tissue Dielectric Properties and Anatomy: A Computational Study"; Phys Med Biol., Sep. 21, 2015, 60(18):7339-7357.

Wi, et al.; "Real-time conductivity imaging of temperature and tissue property changes during radiofrequency ablation: An ex vivo model using weighted frequency difference," Bioelectromagnetics, 36(4):277-286 (Apr. 2015), Epub Mar. 16, 2015.

Windhoff, et al.; "Electric field calculations in brain stimulation based on finite elements: an optimized processing pipeline for the generation and usage of accurate individual head models."; Human Brain Mapping, 34(4): 923-935 (Apr. 2013).

OPTIMIZING POSITIONS OF ELECTRODES FOR APPLYING TUMOR TREATING FIELDS (TTFIELDS) BY ADDING A DIPOLE TO A 3D MODEL

CROSS REFERENCE TO RELATED APPLICATIONS

This application is a continuation of U.S. patent application Ser. No. 16/222,042, filed Dec. 17, 2018, which is a divisional of U.S. patent application Ser. No. 15/336,660 filed Oct. 27, 2016, which claims the benefit of U.S. Provisional Applications 62/247,314 filed Oct. 28, 2015, and 62/294,372 filed Feb. 12, 2016, each of which is incorporated herein by reference in its entirety.

BACKGROUND

Tumor Treating Fields, or TTFields, are low intensity (e.g., 1-3 V/cm) alternating electric fields within the intermediate frequency range (100-300 kHz). This non-invasive treatment targets solid tumors and is described in U.S. Pat. No. 7,565,205, which is incorporated herein by reference in its entirety. TTFields disrupt cell division through physical interactions with key molecules during mitosis. TTFields therapy is an approved mono-treatment for recurrent glioblastoma, and an approved combination therapy with chemotherapy for newly diagnosed patients. These electric fields are induced non-invasively by transducer arrays (i.e., arrays of electrodes) placed directly on the patient's scalp. TTFields also appear to be beneficial for treating tumors in other parts of the body.

TTFields are established as an anti-mitotic cancer treatment modality because they interfere with proper microtubule assembly during metaphase and eventually destroy the cells during telophase and cytokinesis. The efficacy increases with increasing field strength and the optimal frequency is cancer cell line dependent with 200 kHz being the frequency for which inhibition of glioma cells growth caused by TTFields is highest. For cancer treatment, non-invasive devices were developed with capacitively coupled transducers that are placed directly at the skin region close to the tumor. For patients with Glioblastoma Multiforme (GBM), the most common primary, malignant brain tumor in humans, the device for delivering TTFields therapy is called Optune™.

Because the effect of TTFields is directional with cells dividing parallel to the field affected more than cells dividing in other directions, and because cells divide in all directions, TTFields are typically delivered through two pairs of transducer arrays that generate perpendicular fields within the treated tumor. More specifically, for the Optune system one pair of electrodes is located to the left and right (LR) of the tumor, and the other pair of electrodes is located anterior and posterior (AP) to the tumor. Cycling the field between these two directions (i.e., LR and AP) ensures that a maximal range of cell orientations is targeted.

In-vivo and in-vitro studies show that the efficacy of TTFields therapy increases as the intensity of the electric field increases. Therefore, optimizing array placement on the patient's scalp to increase the intensity in the diseased region of the brain is standard practice for the Optune system. To date, array placement optimization is done either by rule of thumb (e.g., placing the arrays on the scalp as close to the tumor as possible) or using the NovoTal™ system. NovoTal™ uses a limited set of measurements describing the geometry of the patient's head, the tumor dimensions and its location to find an optimal array layout. The measurements used as input for NovoTal™ are manually derived from the patient MRIs by the physician. The NovoTal™ optimization algorithm relies on a generic understanding of how the electric field distributes within the head as a function of the positions of the array, and does not take account for variations in the electrical property distributions within the heads of different patients. These variations may influence the field distribution within the head and tumor, leading to situations in which the layouts that NovoTal™ recommends are sub-optimal.

SUMMARY OF THE INVENTION

One aspect of the invention is directed to a first method of optimizing positions of a plurality of electrodes placed on a subject's body, wherein the electrodes are used to impose an electric field in target tissue within an anatomic volume. The first method comprising the steps of obtaining electrical conductivity or resistivity measurements in the anatomic volume, and generating a 3D map of electrical conductivity or resistivity of the anatomic volume directly from the obtained electrical conductivity or resistivity measurements, without segmenting the anatomic volume into tissue types. This method also includes the steps of identifying a location of the target tissue within the anatomic volume, and determining positions for the electrodes based on the 3D map of electrical conductivity or resistivity generated in the generating step and the location of the target tissue identified in the identifying step.

Some embodiments of the first method further comprise the steps of affixing the electrodes to the subject's body at the positions determined in the determining step, and applying electrical signals between the electrodes subsequent to the affixing step, so as to impose the electric field in the target tissue.

In some embodiments of the first method, the measurements obtained in the obtaining step represent the diffusion of molecules. In some embodiments of the first method, the obtaining step comprises acquiring Mill data using diffusion weighted imaging. In some embodiments of the first method, the obtaining step comprises acquiring Mill data using customized multi echo gradient sequences.

In some embodiments of the first method, the obtaining step comprises acquiring MM data using diffusion tensor imaging. Optionally, in these embodiments, the step of acquiring Mill data using diffusion tensor imaging comprises a direct mapping method that assumes a linear relationship between eigenvalues of diffusion and conductivity tensors, $\sigma v = s \cdot dv$, where $\sigma v$ and $dv$ are the with eigenvalues of the conductivity and the diffusion respectively. Optionally, in these embodiments, the step of acquiring Mill data using diffusion tensor imaging comprises a volume normalized method in which a geometric mean of conductivity tensors eigenvalues in each volume element in the anatomic volume are matched locally to specific isotropic conductivity values of a tissue type to which the volume element belongs.

In some embodiments of the first method, the anatomic volume comprises white matter and grey matter of a brain.

In some embodiments of the first method, the anatomic volume is a brain, and the determination of positions for the electrodes is based on a composite model in which the 3D map of electrical conductivity or resistivity of the brain is surrounded by a model of a first shell having a first constant conductivity. In these embodiments, the model of the first shell may represent a scalp, a skull, and CSF, taken together.

Alternatively, in these embodiments, the model of the first shell may represent CSF, the composite model further includes a second shell that represents a skull, the second shell having a second constant conductivity, and the composite model further includes a third shell that represents a scalp, the third shell having a third constant conductivity. In these embodiments, the step of determining positions for the electrodes may comprise adding a dipole to the composite model at a location that corresponds to the target tissue and selecting external positions at which a potential attributable to the dipole is maximum.

In some embodiments of the first method, the step of determining positions for the electrodes comprises calculating positions for the electrodes that will provide a maximum intensity of the electric field in the target tissue. In some embodiments of the first method, in the generating step, the 3D map has a resolution that is higher than 1 mm×1 mm×1 mm. In some embodiments of the first method, the step of generating a 3D map comprises generating a simple geometric object representing the anatomic volume.

In some embodiments of the first method, the step of generating a 3D map comprises classifying a tissue type for each volume element based on a fractional anisotropy. In some embodiments of the first method, the step of generating a 3D map comprises classifying a tissue type for each volume element based on a mean conductivity. In some embodiments of the first method, the step of generating a 3D map comprises matching geometric means of conductivity tensors' eigenvalues to specific isotropic reference values.

Another aspect of the invention is directed to a second method of creating a model of a mammal's head. The head includes brain tissue, CSF, a skull, and a scalp. This method comprises the steps of modeling a region of the head that corresponds to brain tissue using a 3D set of conductivity tensors, and modeling the CSF, the skull, and the scalp using at least one shell having a constant conductivity.

In some embodiments of the second method, the step of modeling the region of the head that corresponds to brain tissue using a 3D set of conductivity tensors is implemented without identifying boundaries between different types of a healthy brain tissue.

In some embodiments of the second method, the 3D set of conductivity tensors is obtained using MRI. In some of these embodiments, the 3D set of conductivity tensors is derived from a diffusion tensor imaging dataset.

In some embodiments of the second method, the step of modeling the CSF, the skull, and the scalp comprises the steps of modeling the CSF as a first shell disposed outside the brain tissue and in contact with the brain tissue, the first shell having a first constant conductivity; modeling the skull as a second shell disposed outside the CSF and in contact with the CSF, the second shell having a second constant conductivity; and modeling the scalp as a third shell disposed outside the skull and in contact with the skull, the third shell having a third constant conductivity.

In some embodiments of the second method, the step of modeling the CSF, the skull, and the scalp comprises the step of modeling the CSF, the skull, and the scalp, taken together, as a single shell disposed outside the brain tissue and in contact with the brain tissue, the single shell having a constant conductivity.

Some embodiments of the second method further comprise the steps of identifying a location of a target tissue within the brain tissue, and determining positions for a plurality of electrodes based on the location of the target tissue identified in the identifying step, the 3D set of conductivity tensors, and the conductivity of the at least one shell. Optionally, these embodiments further comprise the steps of affixing the electrodes to the mammal's head at the positions determined in the determining step, applying electrical signals between the electrodes subsequent to the affixing step, so as to impose an electric field in the target tissue. Optionally, in these embodiments, the step of determining positions for the electrodes comprises modeling a dipole at a location that corresponds to the target tissue and selecting positions at which a potential attributable to the dipole is maximum. Optionally, in these embodiments, the step of determining positions for the electrodes comprises calculating positions for the electrodes that will provide optimal combined treatment specifications in the target tissue.

In some embodiments of the second method, the step of modeling a region using a 3D set of conductivity tensors comprises classifying a tissue type for each volume element based on a fractional anisotropy. In some embodiments of the second method, the step of modeling a region using a 3D set of conductivity tensors comprises classifying a tissue type for each volume element based on a mean conductivity. In some embodiments of the second method, the step of modeling a region using a 3D set of conductivity tensors comprises matching geometric means of conductivity tensors' eigenvalues to specific isotropic reference values.

Another aspect of the invention is directed to a third method of optimizing positions of a plurality of electrodes placed on a subject's body. The electrodes are used to impose an electric field in target tissue within an anatomic volume. The third method comprises the steps of generating a 3D map of electrical conductivity or resistivity of the anatomic volume; identifying a location of the target tissue within the anatomic volume; adding a dipole to the 3D map at a location that corresponds to the target tissue; and determining positions for the electrodes that maximize a potential attributable to the dipole based on the 3D map of electrical conductivity or resistivity generated in the generating step and the location of the dipole.

In some instances of the third method, the location at which the dipole is added corresponds to a center of the target tissue. Optionally, the added dipole is aligned with a direction of an expected electric field.

Some instances of the third method further comprise the steps of affixing the electrodes to the subject's body at the positions determined in the determining step; and applying electrical signals between the electrodes subsequent to the affixing step, so as to impose the electric field in the target tissue. Optionally, in these instances, the location at which the dipole is added corresponds to a center of the target tissue, and the added dipole is aligned with a direction of an expected electric field.

Some instances of the third method further comprise obtaining electrical conductivity or resistivity measurements in the anatomic volume. The 3D map of electrical conductivity or resistivity of the anatomic volume is generated directly from the obtained electrical conductivity or resistivity measurements, without segmenting the anatomic volume into tissue types. In these instances, the obtaining may include acquiring MRI data using diffusion weighted imaging, acquiring MRI data using customized multi echo gradient sequences, or acquiring MM data using diffusion tensor imaging.

DESCRIPTION OF THE PREFERRED EMBODIMENTS

One approach to overcoming the limitations of the NovoTal™ system is to optimize array layouts based on accurate calculations of the electric field distributions within the patient's head as a function of array position. The patient can be a human or other type of mammal or other animals. This can be done by constructing realistic computational models describing the distribution of conductivity within the patient's head. This can be achieved using MRI data. However, to date, deriving such realistic computational head models is time consuming and requires a lot of manual intervention. The reason for this is that the models are obtained by segmenting the MR images into various tissue types and assigning representative conductivity values to each tissue type. Although the segmentation of the outer layers of the head, like the scalp, skull and cerebrospinal fluid (CSF) might be achieved with standard software without major difficulties, the cortical tissues have very complex geometric patterns and are much more complicated to process.

Although automatic and semi-automatic algorithms for segmenting the cortical tissues do exist, their performance is generally not sufficient for creating detailed models. Furthermore, the performance of cortical tissue segmentation algorithms deteriorates further when patient MRIs with large distortions due to tumor tissue and edema are present in the brain, and therefore extensive user intervention is required for this task. Hence, creating realistic computational head models of patients through rigorous segmentation of MR images is extremely labor-intensive and time consuming.

This application describes a work-flow for creating realistic head models for simulating TTFields with minimal user intervention, as well as details on how these head models can be used to optimize TTFields array layouts on patients. In the approach presented here, conductivity values in the head model are determined directly from MRI-based conductivity measurements. Therefore, the need for complex and accurate segmentation is removed, reducing the time and human labor required to create a computational head model of a patient. Once the realistic model has been constructed, the optimization can be performed in a fully or semi-automatic manner using a sequence of algorithms that is also described herein.

For convenience, this description is divided into three parts: Part 1 provides a detailed description of methods for creating realistic head models for TTFields simulations from MRI data with minimal user intervention. Part 2 provides a detailed description on how to optimize TTFields array positions using the model created in part 1. And part 3 describes proof of concept for the creation of realistic head models for TTFields simulations with minimal user intervention, using simple convex hulls to model the outer layers and a conductivity map to model the brain.

Figure 1:
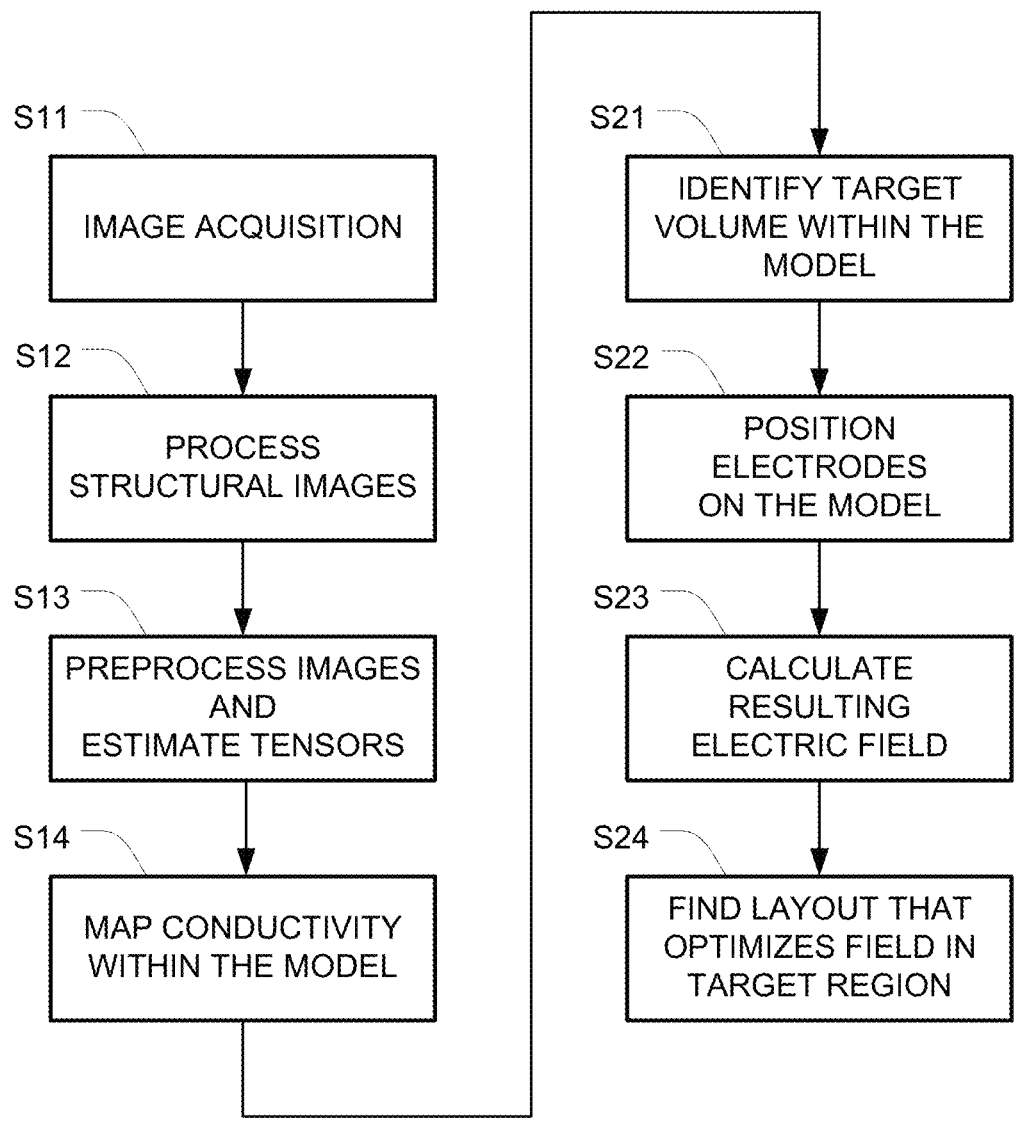
FIG. 1 is a flowchart of one example for creating a model of a head and optimizing the electric field using that model.

FIG. 1 is a flowchart of one example for creating the model (in steps S11-S14) and optimizing the electric field using that model (steps S21-S24).

Part 1: Creation of a Realistic Computational Phantom from MM Data.

Creating an accurate computational phantom preferably involves accurately mapping the electric properties (e.g., conductivity, resistivity) at each point within the computational phantom. One traditional method for creating computational phantoms involves segmentation of the head into different tissue types with distinct isotropic electric properties. When building a model using this method, it is important to accurately identify the boundaries of each tissue type in 3D space so that the electric properties for each tissue type are mapped accurately into the model.

The embodiments described herein overcome the need for rigorous segmentation by using MM sequences such as Diffusion Weighted Imaging (DWI), Diffusion Tensor Imaging (DTI), or customized multi echo gradient sequences (GRE) to directly estimate the electric properties at each point in 3D space. Mapping the electric properties directly using MRI sequences reduces the need for accurate tissue segmentation because the electric properties of every point are defined directly from the MRI, and not from the tissue type to which they are assigned to during the segmentation. Therefore, the segmentation process can be simplified or even eliminated without compromising the accuracy of the computational phantom. Note that while the embodiments described herein discuss mapping conductivity, alternative embodiments can provide similar results by mapping a different electrical property such as resistivity.

Steps S11-S14 in FIG. 1 depict one example of a set of steps that may be used to generate a computational phantom representing a patient based on MRI conductivity measurements.

Step S11 is the image acquisition step. In this step, both structural data and data from which conductivity maps can be calculated are acquired. Structural data can be obtained for instance from standard $T_1$ and $T_2$ MRI sequences. Conductivity can be obtained using a variety of MRI data acquisition modes such as DWI, DTI or GRE. In order to create a good computational phantom, high resolution images should be obtained. A resolution of at least 1 mm×1 mm×1 mm for both structural and conductivity-related images is preferable. Lower resolution images may be used for one or both of these types of images, but the lower resolution will yield less accurate phantoms.

The data set is preferably inspected and images affected by large artifacts are preferably removed. Preferably some scanner-specific pre-processing is applied. For example, images may be converted from DICOM format to NIFTI. A different step of preprocessing may be to register all images to a standard space (for example the Montreal Neurological Institute, MNI, space). This can be done using readily available software packages including but not limited to FSL FLIRT, and SPM.

Step S12 is the step of processing structural images. As mentioned above, the work-flow presented here utilizes MRI-based conductivity measurements to create the computational phantom. However, structural images may still be used to identify the boundaries of the head, as well as identify regions belonging to specific tissues within the brain in which it might be advantageous to assign typical conductivity values that are not derived from the MRI measurements. For instance, in some cases it may be advantageous to identify (and segment) the skull, scalp and CSF within the images, and assign typical conductivity values to the regions corresponding to these tissues (but still rely on the capital MRI-based measurements for the regions corresponding to the brain).

It is possible to use available software packages to obtain a detailed segmentation of these three tissue types, as well as the ventricles. However, due to the complexity of some of these structures, this still may require significant manual intervention. Therefore, simplified schemes for building the head model may be beneficial. One possibility to downgrade the complexity of creating the phantom is to simplify the geometry representing the outer model layers (scalp, skull and CSF). For example, shells or convex hulls of the outer tissues could be used as a model of those layers. If a rough segmentation of the outer layers is available, the creation of the corresponding convex hull is trivial and can be performed using standard algorithms and software. Another option is for the user to measure the thickness of the three outer layers (scalp, skull and CSF) at a representative region (a region where the transducer arrays might be placed) through examination of the structural image. These measurements can be used to create three concentric shells or layers which represent the scalp, skull, and the CSF. These layers might be obtained by deforming a default oval structure, which could be a default convex hull of a scalp segmentation.

Steps S13 and S14 both deal with processing of DTI images. Step S13 is the step of preprocessing of images and tensor estimation. DTI measurements involve acquisition of multiple images acquired with different imaging conditions. Each image is characterized by its gradient direction and b-value. For processing DTI images, the gradient directions and b-values first need to be extracted. This can be performed using standard software. Once the gradient directions and b-values have been extracted, the images are preferably corrected for distortions which arise from sample motion (e.g., head movements) as well as from distortion to the Mills that arise from eddy currents generated during data acquisition. In addition, the images are preferably registered to overlap with the structural images discussed in the previous stage. Correction of distortions and registration can be performed using standard software packages. After this preprocessing has been completed, the diffusion tensors at each point in relevant regions of the model can be estimated.

Many software bundles for deriving the diffusion tensors from DTI images exist. For example, A Hitchhiker's Guide to Diffusion Tensor Imaging by J. M. Soares et al., frontiers in Neuroscience, vol. 7, article 31, p. 1-14, doi: 10.3389/fnins.2013.00031, 2013 includes a detailed summary of available software for the estimation of the tensors and also for preprocessing of DTI. Two options for deriving the diffusion tensors from DTI images were tested. The first option uses the FSL diffusion toolbox for correction and registration of the images and calculating the principal directions (eigenvectors), principal diffusivities (eigenvalues), and the fractional anisotropy. The second option was to use the DIFFPREP module from the Tortoise software in order to perform the motion and eddy current distortion correction with B-matrix reorientation. Then the DIFFCALC module can be used for the estimation of the diffusion tensor in each voxel and for the computation of tensor-derived quantities. In both software packages it is possible to reorient the data set with B-matrix reorientation to a standard frame of reference, which naturally is the structural image.

Step S14 is the step of mapping conductivity within the computational phantom. In this step, conductivity values are mapped to each volume element within the computational phantom. In regions belonging to tissue types where the segmentation is sufficiently accurate (e.g., the skull or CSF), representative isotropic conductivity values for each tissue type may be assigned. In other regions, conductivity values are assigned based on the MRI-based conductivity measurements, such as DTI.

Deriving conductivity values from DTI data follows the proposition that the conductivity tensors share the same eigenvectors as the effective diffusion tensor. Once the diffusion tensor has been estimated for each volume element that was imaged, an estimate of the conductivity tensors can be formed using any suitable approach, some of which are described in detail in How the Brain Tissue Shapes the Electric Field Induced by Transcranial Magnetic Stimulation by A. Opitz et al. Neuroimage, vol. 58, no. 3, pp. 849-59, October 2011. For example, one suitable method is called direct mapping (dM), which assumes a linear relationship between the eigenvalues of the diffusion and conductivity tensors, i.e., $\sigma_v = s \cdot d_v$, where $\sigma_v$ and $d_v$ are the v-th eigenvalues of the conductivity and the diffusion respectively. Different assumptions on the scaling factor can be used, whereas also an adapted scaling factors can be applied following. See e.g., EEG Source Analysis of Epileptiform Activity Using a 1 mm Anisotropic Hexahedra Finite Element Head Model by M. Rullmann et al. NeuroImage 44, 399-410 (2009). Another suitable method is the volume normalized (vN) method in which the geometric mean of the conductivity tensor's eigenvalues in each volume element in the brain are matched locally to the specific isotropic conductivity values of the tissue type to which the element belongs. See e.g., Influence of Anisotropic Electrical Conductivity in White Matter Tissue on the EEG/MEG Forward and Inverse Solution—A High-Resolution Whole Head Simulation Study, by D. Güllmar, NeuroImage 51, 145-163 (2010).

Both of these methods could be used to map conductivity to the relevant regions (mainly cortical region) within the computational phantom. However, the vN method requires a higher degree of accuracy in the segmentation, as conductivity values are mapped at each volume element using information about the tissue type in that area. Therefore, assigning a volume element to the wrong tissue type would result in an error in the conductivity map within the computational phantom. On the other hand, for the dM method the conductivity values are assigned to all elements using the same linear relationship regardless of the tissue type at the area. Therefore, dM of DTI data may be more useful than the vN mapping of DTI data for simplifying the pipeline for creating computational phantoms for TTFields simulations. Note, however, that the constant scaling factor in dM may only lead to accurate values in the healthy tissues, and may be less than optimal for the tumor tissues.

Alternative mapping methods could also be applied. For example, in order to overcome the limitation of the vN method (a segmentation needs to be present to be able to assign each volume element to a specific tissue type), the tissue type of the volume element could also be classified by its fractional anisotropy, mean conductivity, or other related measures. Alternatively, the geometric mean of the conductivity tensor's eigenvalues could be matched to a specific isotropic reference value. This would be a general way to segment or classify tissue types (possibly even creating a full model) only from DTI data. Note that when the fractional anisotropy (or any other measure that can be derived from the conductivity data) is found, then the neighboring elements are preferably checked to avoid outliers (for example, to eliminate a GM point that was identified inside the WM).

Part 2: Optimization of TTFields Array Positions Using Realistic Head Models

Optimization of array layouts means finding the array layout that optimizes the electric field within the diseased regions of the patient's brain (tumor). This optimization may be implemented by performing the following four steps: (S21) identifying the volume targeted for treatment (target volume) within the realistic head model; (S22) automatically placing transducer arrays and setting boundary conditions on the realistic head model; (S23) calculating the electric field that develops within the realistic head model once arrays have been placed on the realistic head model and boundary conditions applied; and (S24) running an optimization algorithm to find the layout that yields optimal electric field distributions within the target volume. A detailed example for implementing these four steps is provided below.

Step S21 involves locating the target volume within the realistic head model (i.e., defining a region of interest). A first step in finding a layout that yields optimal electric field distributions within the patient's body is to correctly identify the location and target volume, in which the electric field should be optimized.

In some embodiments, the target volume will be either the Gross Tumor Volume (GTV) or the Clinical Target Volume (CTV). The GTV is the gross demonstrable extent and location of the tumor, whereas the CTV includes the demonstrated tumors if present and any other tissue with presumed tumor. In many cases the CTV is found by defining a volume that encompasses the GTV and adding a margin with a predefined width around the GTV.

In order to identify the GTV or the CTV, it is necessary to identify the volume of the tumor within the MRI images. This can be performed either manually by the user, automatically, or using a semi-automatic approach in which user-assisted algorithms are used. When performing this task manually, the MRI data could be presented to a user, and the user could be asked to outline the volume of the CTV on the data. The data presented to the user could be structural MRI data (e.g., $T_1$, $T_2$ data). The different MRI modalities could be registered onto each other, and the user could be presented with the option to view any of the datasets, and outline the CTV. The user could be asked to outline the CTV on a 3D volumetric representation of the MRIs, or the user could be given the option of viewing individual 2D slices of the data, and marking the CTV boundary on each slice. Once the boundaries have been marked on each slice, the CTV within the anatomic volume (and hence within the realistic model) can be found. In this case, the volume marked by the user would correspond to the GTV. In some embodiments, the CTV could then be found by adding margins of a predefined width to the GTV. Similarly, in other embodiments, the user might be asked to mark the CTV using a similar procedure.

An alternative to the manual approach is to use automatic segmentation algorithms to find the CTV. These algorithms perform automatic segmentation algorithms to identify the CTV using either the structural MM data, or possibly the DTI data. Note that DTI data can be used for segmentation for this purpose because the diffusion tensor within the tumor (and any edema region) will be different from its surroundings.

However, as mentioned above, current fully automatic segmentation algorithms may not be sufficiently stable. Therefore, semi-automatic segmentation approaches of the MRI data may be preferable. In an example of these approaches, a user iteratively provides input into the algorithm (e.g., the location of the tumor on the images, roughly marking the boundaries of the tumor, demarcating a region of interest in which the tumor is located), which is then used by a segmentation algorithm. The user may then be given the option to refine the segmentation to gain a better estimation of the CTV location and volume within the head.

Whether using automatic or semi-automatic approaches, the identified tumor volume would correspond with the GTV, and the CTV could then be found automatically by expanding the GTV volume by a pre-defined amount (e.g., defining the CTV as a volume that encompasses a 20 mm wide margin around the tumor).

Note that in some cases, it might be sufficient for the user to define a region of interest in which they want to optimize the electric field. This region of interest might be for instance a box volume, a spherical volume, or volume of arbitrary shape in the anatomic volume that encompasses the tumor. When this approach is used, complex algorithms for accurately identifying the tumor may not be needed.

Step S22 involves automatically calculating the position and orientation of the arrays on the realistic head model for a given iteration. Each transducer array used for the delivery of TTFields in the Optune™ device comprise a set of ceramic disk electrodes, which are coupled to the patient's head through a layer of medical gel. When placing arrays on real patients, the disks naturally align parallel to the skin, and good electrical contact between the arrays and the skin occurs because the medical gel deforms to match the body's contours. However, virtual models are made of rigidly defined geometries. Therefore, placing the arrays on the model requires an accurate method for finding the orientation and contour of the model surface at the positions where the arrays are to be placed, as well as finding the thickness/geometry of the gel that is necessary to ensure good contact of the model arrays with the realistic patient model. In order to enable fully automated optimization of field distributions these calculations have to be performed automatically.

A variety of algorithms to perform this task may be used. The steps of one such algorithm recently devised for this purpose are set forth below.

a. Define the position at which the central point of the transducer array will be placed on the model head. The position could be defined by a user or as one of the steps in the field optimization algorithm which are discussed in step S24.

b. Using the input from step (a) in conjunction with knowledge about the geometry of the disks and how the disks are arranged in the array, calculate the approximate positions of the centers of all disks in the transducer array within the model.

c. Calculate the orientations of the surface of the realistic model at the positions where the disks are to be placed. The calculation is performed by finding all points on the computational phantom skin that are within a distance of one disk radius from the designated center of the disk. The coordinates of these points are arranged into the columns of a matrix, and singular value decomposition performed on the matrix. The normal to the model skin is then the eigenvector that corresponds to the smallest eigenvalue found.

d. For each disk in the transducer array: calculate the thickness of the medical gel that is required to ensure good contact between the disks and the patient's body. This is done by finding the parameters for a cylinder with its height oriented parallel to the skin surface normal. The cylinder is defined with a radius equal to the radius of the disks, and its height set to extend a pre-determined amount (this is a pre-determined constant) beyond the points on the skin used to find the normal. This results in a cylinder that extends at-least the pre-determined amount out from the phantom surface.

e. On the model, create the cylinders described in (d).

f. Through binary logical operations (e.g., subtract head from cylinder) remove from the model the regions of the cylinder that protrude into the realistic model of the patient. The resulting "truncated cylinders" represent the medical gel associated with the transducer arrays g. On the outer side of the "truncated cylinders" place disks that represent the ceramic disks of the transducer arrays.

Step S23 involves calculating the electric field distribution within the head model for the given iteration. Once the head phantom is constructed and the transducer arrays (i.e., the electrode arrays) that will be used to apply the fields are placed on the realistic head model, then a volume mesh, suitable for finite element (FE) method analysis, can be created. Next boundary conditions can be applied to the model. Examples of boundary conditions that might be used include Dirichlet boundary (constant voltage) conditions on the transducer arrays, Neumann boundary conditions on the transducer arrays (constant current), or floating potential boundary condition that set the potential at that boundary so that the integral of the normal component of the current density is equal to a specified amplitude. The model can then be solved with a suitable finite element solver (e.g., a low frequency quasistatic electromagnetic solver) or alternatively with finite difference (FD) algorithms. The meshing, imposing of boundary conditions and solving of the model can be performed with existing software packages such as Sim4Life, Comsol Multiphysics, Ansys, or Matlab. Alternatively, custom computer code that realizes the FE (or FD) algorithms could be written. This code could utilize existing open-source software resources such as C-Gal (for creating meshes), or FREEFEM++(software written in C++ for rapid testing and finite element simulations). The final solution of the model will be a dataset that describes the electric field distribution or related quantities such as electric potential within the computational phantom for the given iteration.

Step 24 is the optimization step. An optimization algorithm is used to find the array layout that optimizes the electric field delivery to the diseased regions of the patient's brain (tumor) for both application directions (LR and AP, as mentioned above). The optimization algorithm will utilize the method for automatic array placement and the method for solving the electric field within the head model in a well-defined sequence in order to find the optimal array layout. The optimal layout will be the layout that maximizes or minimizes some target function of the electric field in the diseased regions of the brain, considering both directions at which the electric field is applied. This target function may be for instance the maximum intensity within the diseased region or the average intensity within the diseased region. It also possible to define other target functions.

There are a number of approaches that could be used to find the optimal array layouts for patients, three of which are described below. One optimization approach is an exhaustive search. In this approach the optimizer will include a bank with a finite number of array layouts that should be tested. The optimizer performs simulations of all array layouts in the bank (e.g., by repeating steps S22 and S23 for each layout), and picks the array layouts that yield the optimal field intensities in the tumor (the optimal layout is the layout in the bank that yields the highest (or lowest) value for the optimization target function, e.g., the electric field strength delivered to the tumor).

Another optimization approach is an iterative search. This approach covers the use of algorithm such as minimum-descent optimization methods and simplex search optimization. Using this approach, the algorithm iteratively tests different array layouts on the head and calculates the target function for electric field in the tumor for each layout. This approach therefore also involves repeating steps S22 and S23 for each layout. At each iteration, the algorithm automatically picks the configuration to test based on the results of the previous iteration. The algorithm is designed to converge so that it maximizes (or minimizes) the defined target function for the field in the tumor.

Yet another optimization approach is based on placing a dipole at the center of the tumor in the model. This approach differs from the other two approaches, as it does not rely on solving field intensity for different array layouts. Rather, the optimal position for the arrays is found by placing a dipole aligned with the direction of the expected field at the center of the tumor in the model, and solving the electromagnetic potential. The regions on the scalp where the electric potential (or possibly electric field) is maximal will be the positions where the arrays are placed. The logic of this method is that the dipole will generate an electric field that is maximal at the tumor center. By reciprocity, if we were able to generate the field/voltage on the scalp that the calculation yielded, then we would expect to obtain a field distribution that is maximal at the tumor center (where the dipole was placed). The closest we can practically get to this with our current system is to place the arrays in the regions where the potential induced by the dipole on the scalp is maximal.

Note that alternative optimization schemes can be used to find an array layout that optimizes the electric field within diseased regions of the brain. For example, algorithms that combine the various approaches mentioned above. As an example of how these approaches may be combined, consider an algorithm in combining the third approach discussed above (i.e., positioning the dipole at the center of the tumor in the model) with the second approach (i.e., the iterative search). With this combination, an array layout is initially found using the dipole at the center of the tumor approach. This array layout is used as input to an iterative search that finds the optimal layout.

Part 3: Proof of Concept that Simplified Head Models can be Constructed and Yield Accurate Results.

Proof of concept was based on modifications to a previously developed realistic human head model that incorporated anisotropic conductivity values of the cortical tissues. This model originated from a healthy subject, so that the tumor had to be represented by a virtual lesion. The phantom has already been used to calculate the electric field distribution following TTFields application.

In order to test the concept, first convex hulls of all tissue types were created, except the ventricles. The cystic tumor in this model was represented by two concentric spheres, an active shell surrounding the necrotic core. It was placed in the right hemisphere close to the lateral ventricle.

Figure 2:
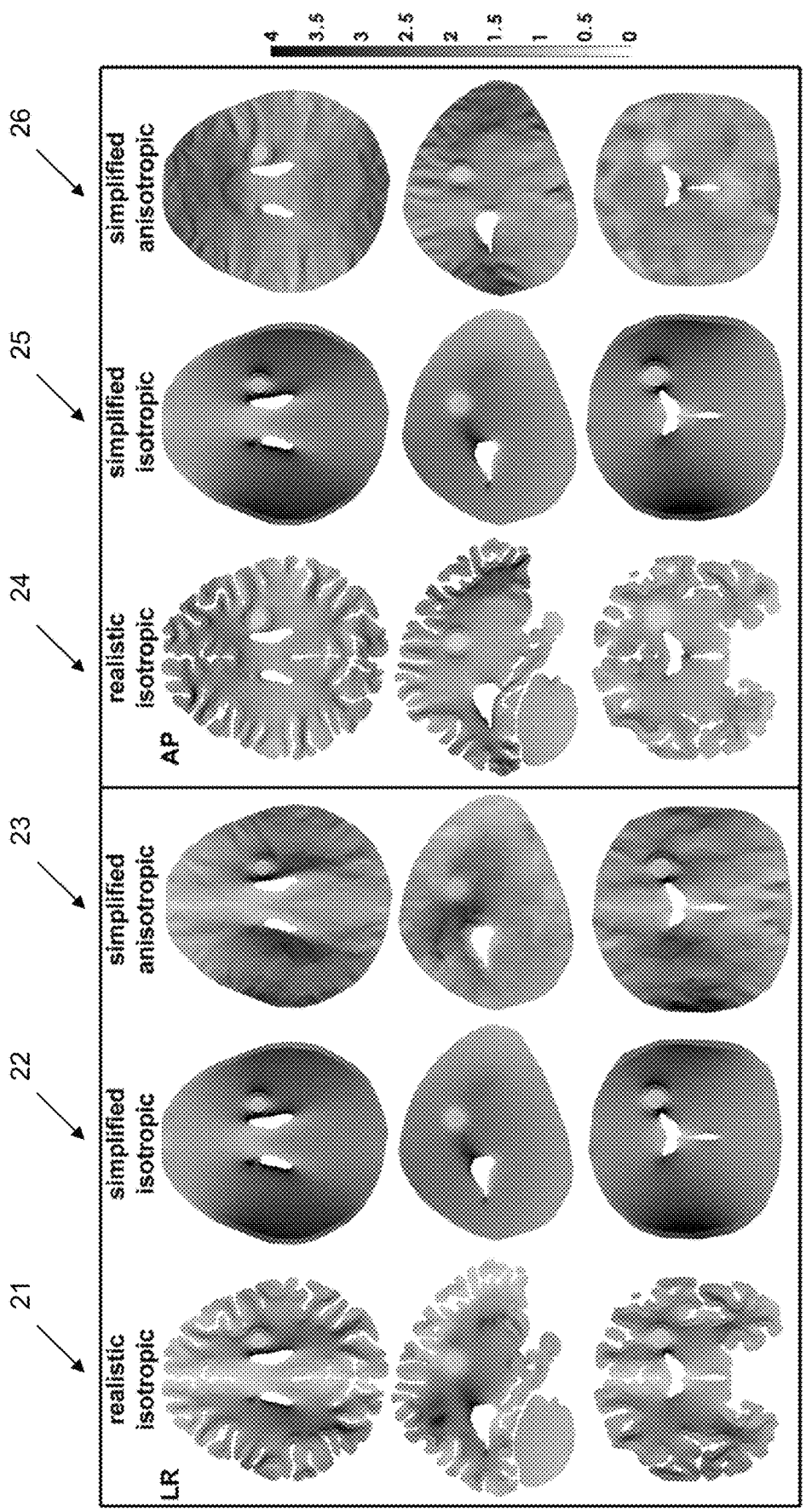
FIG. 2 depicts electric field distributions in various cross-sections through a virtual tumor in three different models created using the same MM data set.

FIG. 2 shows the electric field distribution in various cross-sections through the tumor of three different models created using the same MRI data set. More specifically, FIG. 2 shows the results for both perpendicular configurations used for TTFields treatment: the left and right (LR) array (panels 21-23), and the array in the anterior and posterior (AP) parts of the head (panels 24-26). Panels 21 and 24 show results for the classic modelling approach, the realistic head model, in which the MRI is accurately segmented and representative isotropic dielectric properties of each tissue are assigned to all volume elements belonging to that tissue. Panels 22 and 24 show results for the simplified modeling approach in which tissue types are segmented as convex hulls, and representative isotropic dielectric properties are assigned to each tissue type. Panels 23 and 26 show results of the simplified model in which conductivity values are assigned to each volume element of the cortical tissues (GM, WM, and cerebellum) based on conductivity maps derived from DTI images.

The correlation between the various modeling approaches is strong. More specifically, the TTFields-induced electric field distribution within the brain and tumor of the realistic head model is non-uniform. This means that although the field intensity is highest close to the active transducer arrays, additional hotspots are induced in the center of the head (in tissues with the lower conductivity close to boundaries to which the electric field is perpendicular), as seen in panels 21 and 24. In the isotropic simplified model, as a result of the smooth tissue interfaces, the field distribution is merely decaying away from the transducers. Nonetheless because heterogeneous dielectric properties are used, the "usual" hotspots are seen close to the ventricles and also within the tumor's active shell. Closely observing the field distribution inside the tumor, reveals very similar patterns in the original and the simple isotropic model, as seen in panels 22 and 25. Incorporating anisotropic conductivity tensors in the brain tissues results in even more similar electric field distributions within the brain, as seen in panels 23 and 26. It appears that the gyri are visible as well as some major fiber tracts and the current flow through them becomes notable.

When comparing the average electric field values in the tumor as calculated using the realistic vs the simplified model, the percentage difference for the isotropic models is less than 6%. When the realistic anisotropic model is compared to the simplified anisotropic model, the percentage difference between average field strength in the tumor shell is less than 5%. In both cases the slightly lower values are predicted for the simplified model.

Figure 3:
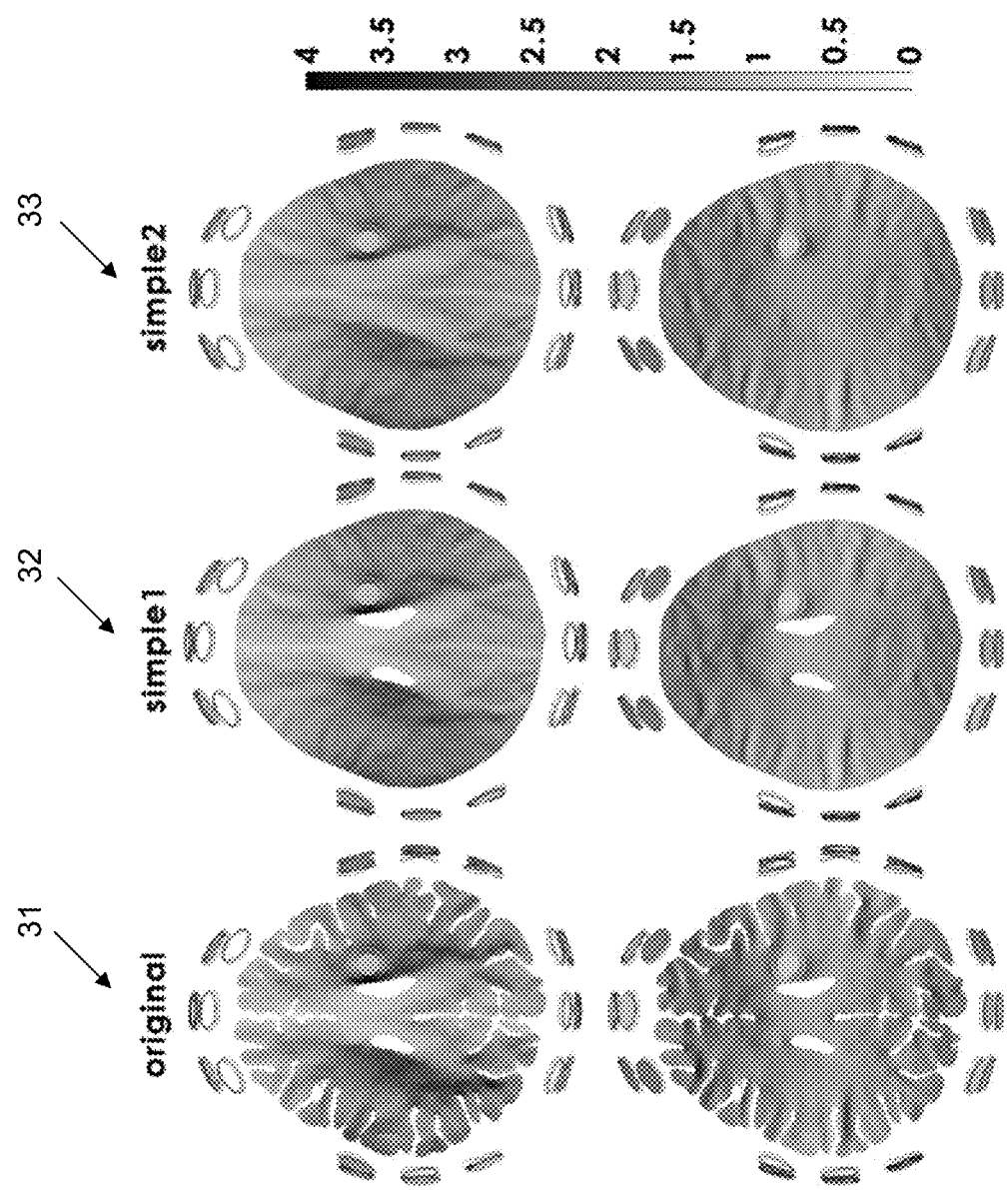
FIG. 3 depicts the electric field distribution for three anisotropic models in one axial slice through the tumor.

In FIG. 3 the electric field distribution is again presented in one axial slice through the virtual tumor. In each of the panels 31-33, the electric field distribution in this axial slice for the LR and AP arrays appears at the top and bottom of the panel, respectively. The original model (panel 31) corresponds to the realistic representation of all tissues with dM anisotropy for the cortical tissues. The simple1 model (panel 32) also uses dM anisotropic conductivity tensors for the cortical tissues (represented by convex hulls) and it employs convex hull or shells of all surfaces except the ventricles, all of which have isotropic conductivity values. The simple2 model (panel 33) is similar to the simple1 model, but a detailed representation of the ventricles is neglected, whereas their presence is accounted for by using anisotropic conductivity tensors derived for this region from the DTI data (for the original and the simple1 model this data was neglected or overwritten by the ventricle segmentation with an isotropic conductivity value). Table 1 compiles the corresponding average field strength values in the brain and the two tumor tissues. Since this virtual lesion is close to the ventricles the field in the tumor is more affected by the ongoing simplification. Still the differences are relatively small, whereas the average field in the tumor induced by the LR array is increased to 114% in the original realistic model (compared to the simple2) model and reduced to 95% in the AP stimulation.

TABLE 1

|  |  | LR | | | AP | | |
| --- | --- | --- | --- | --- | --- | --- | --- |
|  |  | Brain | shell | core | Brain | shell | core |
| avg(E) | original | 1.39 | 1.76 | 0.82 | 1.43 | 1.20 | 0.55 |
| V/cm | simple1 | 1.35 | 1.67 | 0.78 | 1.39 | 1.18 | 0.54 |
|  | simple2 | 1.36 | 1.54 | 0.72 | 1.42 | 1.26 | 0.58 |
| ori/simple1 | | 103% | 105% | 105% | 103% | 102% | 102% |
| ori/simple2 | | 102% | 114% | 114% | 101% | 95% | 95% |

This shows that use of the approaches described herein leads to sufficiently accurate electric field distributions in the head and correct field strength values, while being more time and computationally efficient. Notably, the simplified model should be accurate enough for optimization of electrode placement.

Additional details of the modeling of part 3 will now be discussed, including models in which simple convex hulls or shells are used to model the outer layers and a conductivity map is used to model the brain. These models are able to account for anisotropic conductivity in the cortical tissues by using a tensor representation estimated from Diffusion Tensor Imaging. The induced electric field distribution is compared in the simplified and a realistic head model. The average field strength values in the brain and tumor tissues are generally slightly higher in the realistic head model, with a maximal ratio of 114% for a standard simplified model (when reasonable thickness of layers are assured). It therefore provides a fast and efficient way towards personalized head models with a decreased degree of complexity between tissue interfaces that enables accurate predictions about increased electric field distribution.

This study presents a first approach towards personalized head models which would not need an underlying segmentation of the different head tissues. The method rather uses simple convex hulls to model the outer layers and a conductivity representation of the cortical tissues derived from a Diffusion Tensor Imaging (DTI) dataset.

Figure 4:
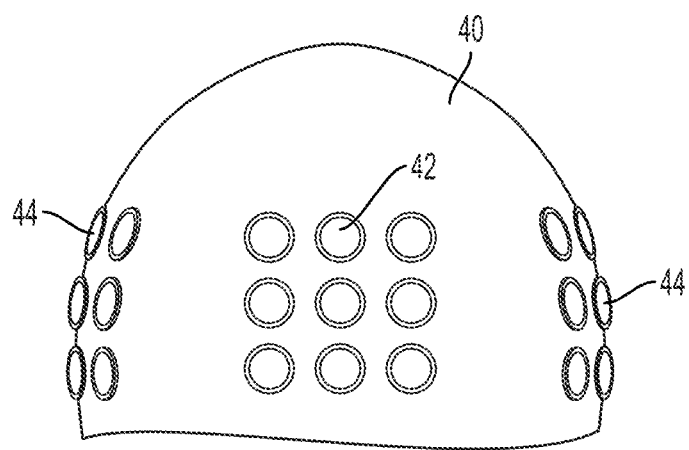
FIG. 4 depicts a front view of the scalp with transducer arrays affixed to the scalp.

A previously developed realistic human head model was used as a baseline model. An MRI dataset of a healthy, young, female was segmented into scalp, skull, cerebrospinal fluid (CSF), gray matter (GM) including the cerebellum, white matter (WM), and ventricles. A virtual tumor located centrally was modelled as two concentric spheres, an inner necrotic core surrounded by an active tumor shell. The Optune™ system with a central symmetric layout was used for all calculations. FIG. 4, which is a front view of the scalp 40 with the Optune™ transducer arrays 42, 44 affixed to the scalp depicts this layout. Note that only three of the four patches are visible in the figure and that neither the eyes nor the ears are represented on the convex hull. The final volume mesh was assembled with Mimics (www.materialise.com).

Isotropic conductivity and permittivity values of the heterogeneous tissues were assumed as in previous studies and anisotropic conductivity tensors of the cortical tissues were estimated from Diffusion Tensor Imaging (DTI) data. Different approaches are assumed for the scaling of the diffusion tensors. In this example, only the direct mapping (dM) approach with the same scaling factor for each voxel was used. Further details are presented in The Electric Field Distribution in the Brain During TTFields Therapy and Its Dependence on Tissue Dielectric Properties and Anatomy: A Computational Study by C. Wenger at al., Phys. Med. Biol., vol. 60, no. 18, pp. 7339-7357, 2015, which is incorporated herein by reference.

Figure 5B:
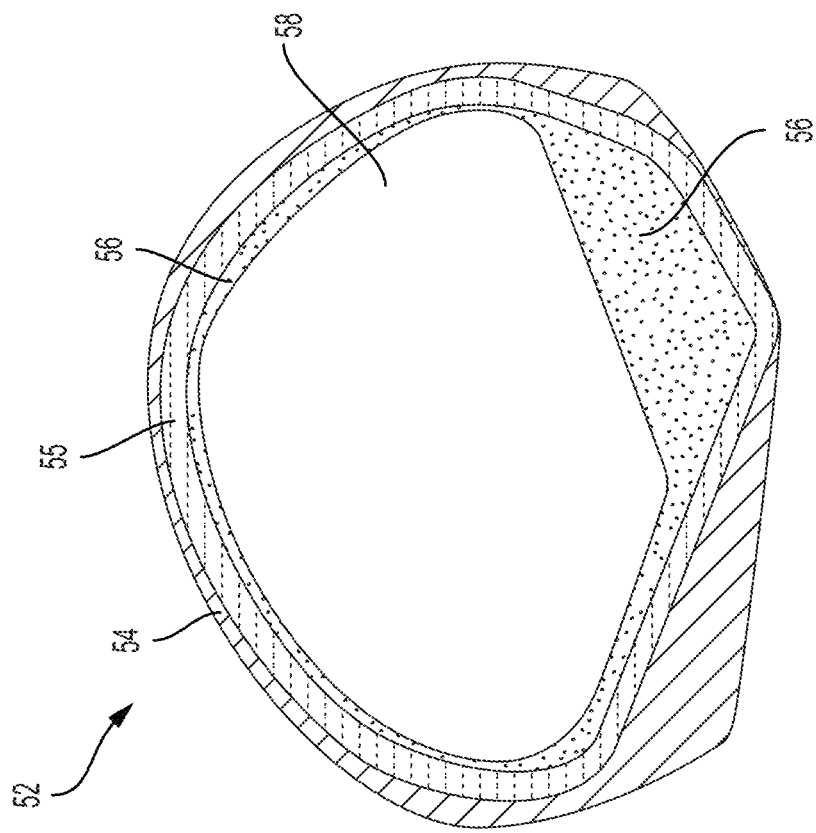
FIGS. 5A and 5B respectively depict a set of shells for two different models.
Figure 5A:
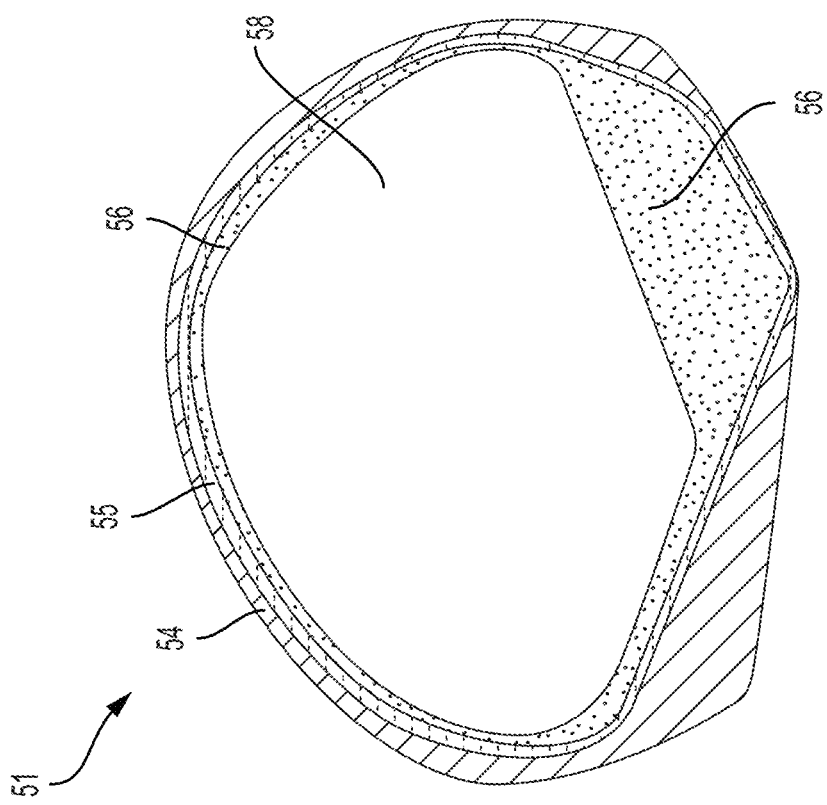
Figure 6B:
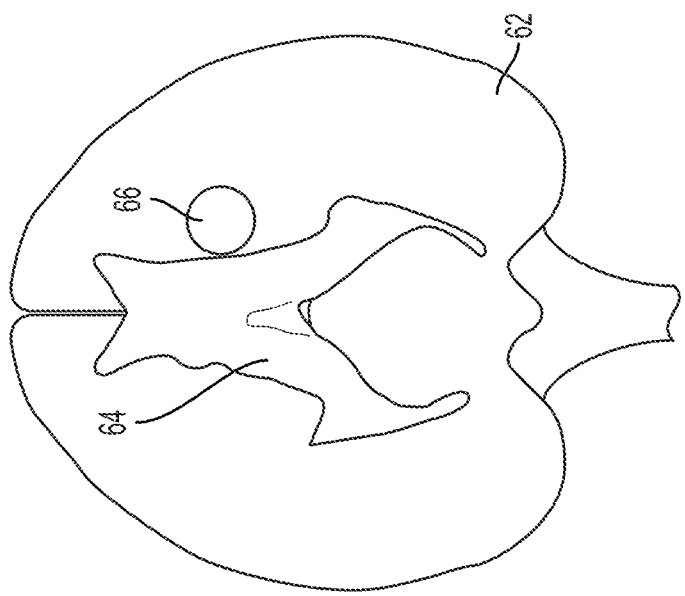
FIGS. 6A and 6B depict side and the top views, respectively, of ventricles and a virtual tumor inside a white matter shell.
Figure 6A:
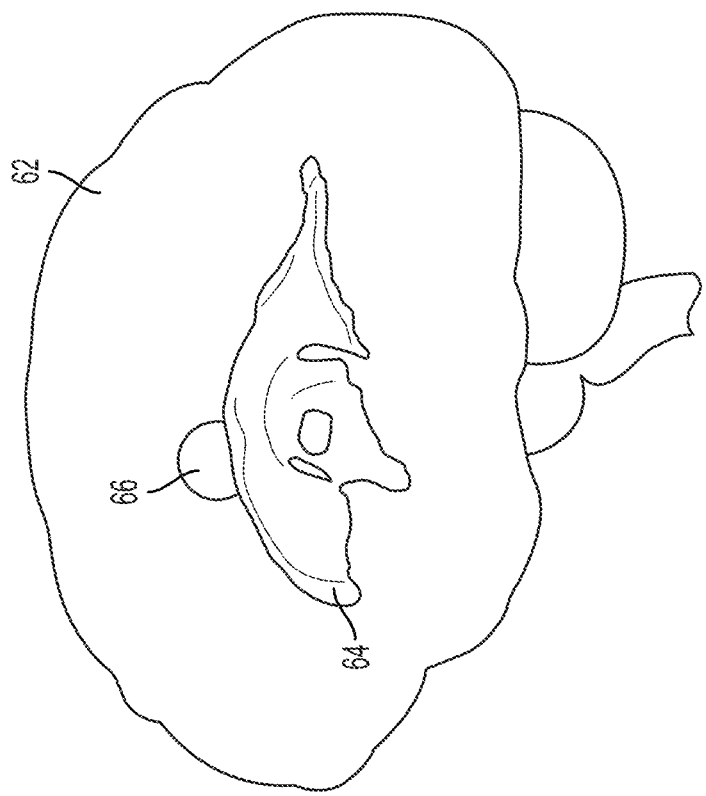

One approach to simplify the model is to use convex hulls of the surface meshes instead of the complex and irregular geometry. In this study, convex hulls were created with MeshLab (http://meshlab.sourceforge.net/). The GM and the cerebellum were approximated as a single envelope, the WM, the scalp, the skull, and the CSF were represented by one convex hull each. FIGS. 5A and 5B depict the arrangement of the convex hulls (i.e., shells) for two similar simplified models, called SHM1 (51) and SHM2 (52) respectively. In both models, the convex hulls include the skull 54, the CSF 55 the grey matter (GM) 56, and the white matter (WM) 58. Note that the CSF 55 in SHM1 51 is very thin compared to the CSF 55 in SHM2 52. FIGS. 6A and 6B depict side and top views, respectively, of the ventricles 64 and the tumor 66 inside the WM convex hull 62. The ventricles and the tumor tissues (active shell and necrotic core) remained unchanged.

Four different simple head models were developed (SHM1-SHM4). The first, SHM1, consists of the mentioned convex hulls which results in very different tissue volumes compared to RHM. The WM is the innermost of the altered tissues which is highly affected by applying a convex envelope with a more than doubled tissue volume. This affects the surrounding tissues. The GM has a smaller volume in SHM1. The envelope over the GM gyri and the whole cerebellum reduces the volume of the CSF in SHM1. The only tissue with a slightly bigger volume in SHM1 compared to RHM is the skull which, in turn, results in a reduced volume of the scalp. Still, it shall be noted that the thickness of the scalp and skull layers underneath the transducers are very similar in SHM1 and RHM, i.e., on average (of all 36 transducers) the ratio between layer thickness of RHM vs SHM1 is 102% in the scalp and 110% in the skull. Nonetheless, this ratio is 270% for the CSF. Thickness was estimated with the volume of intersecting cylinders, i.e., a cylinder was created extending the transducer and then the intersecting volume with the next tissue surface was calculated. Thus, the higher volume of the CSF cylinders of RHM is attributed to the additional volume resulting from the sulci instead of a plane GM as in SHM1.

A second simple model, SHM2, was created to reduce these discrepancies, i.e., the altered tissue volumes and the minimal CSF thickness in SHM1 (as seen in FIG. 5A). SHM2 resulted from scaling meshes in Mimics: the WM and GM simultaneously by a factor of 0.97 followed by scaling the CSF with a factor of 0.995. This resulted in decreased differences of layer thickness for SHM2 compared to RHM of 102% for the scalp, 100% for the skull and 128% for the CSF. These two models were first solved as isotropic and anisotropic models and compared to the RHM results. The estimation of the conductivity tensors with DTI data remained unchanged. Note that in RHM all DTI data outside the GM boundary was disregarded. The diffusion information for all additional voxels that are part of the GM convex hull in SHM1 and SHM2 were added.

SHM3 is a simpler model that only uses one convex hull for the cortical tissues, leaving out the boundary between WM and GM. As a last simplification step, SHM4 further cuts the ventricles and only works with the conductivity data derived from DTI, instead of an isotropic CSF-filled chamber in all other models.

In order to calculate the electric field distribution, the finite element (FE) software Comsol Multiphysics (http://www.comsol.com) was used to solve the quasi-static approximation of the Maxwell equations in the frequency domain with 200 kHz. Isotropic and anisotropic material properties were already discussed. Boundary conditions assumed continuity of the normal component at inner boundaries, electric insulation at outer boundaries. TTFields activation was simulated with Floating Potential conditions with 100 mA for each active transducer.

The results of the study are as follows. Each model setup (type of model, isotropic or dM representation of the brain conductivities) is solved for both array field directions, LR and AP.

The first simulations were carried out with the SHM1 model and the isotropic and anisotropic solutions were compared to those of the RHM model. This initial simplified model, SHM1, with its thin CSF produces high electric field strength values in the brain and tumor tissues (Table 2). When adapting the CSF thickness introduced by SHM2, the obtained average field strength values are very similar and slightly decreased in the tumor compared to RHM. As presented in Table 2 the highest increase is 107% reported for the average field strength in the tumor shell under LR activation and isotropic conductivities.

Figure 7:
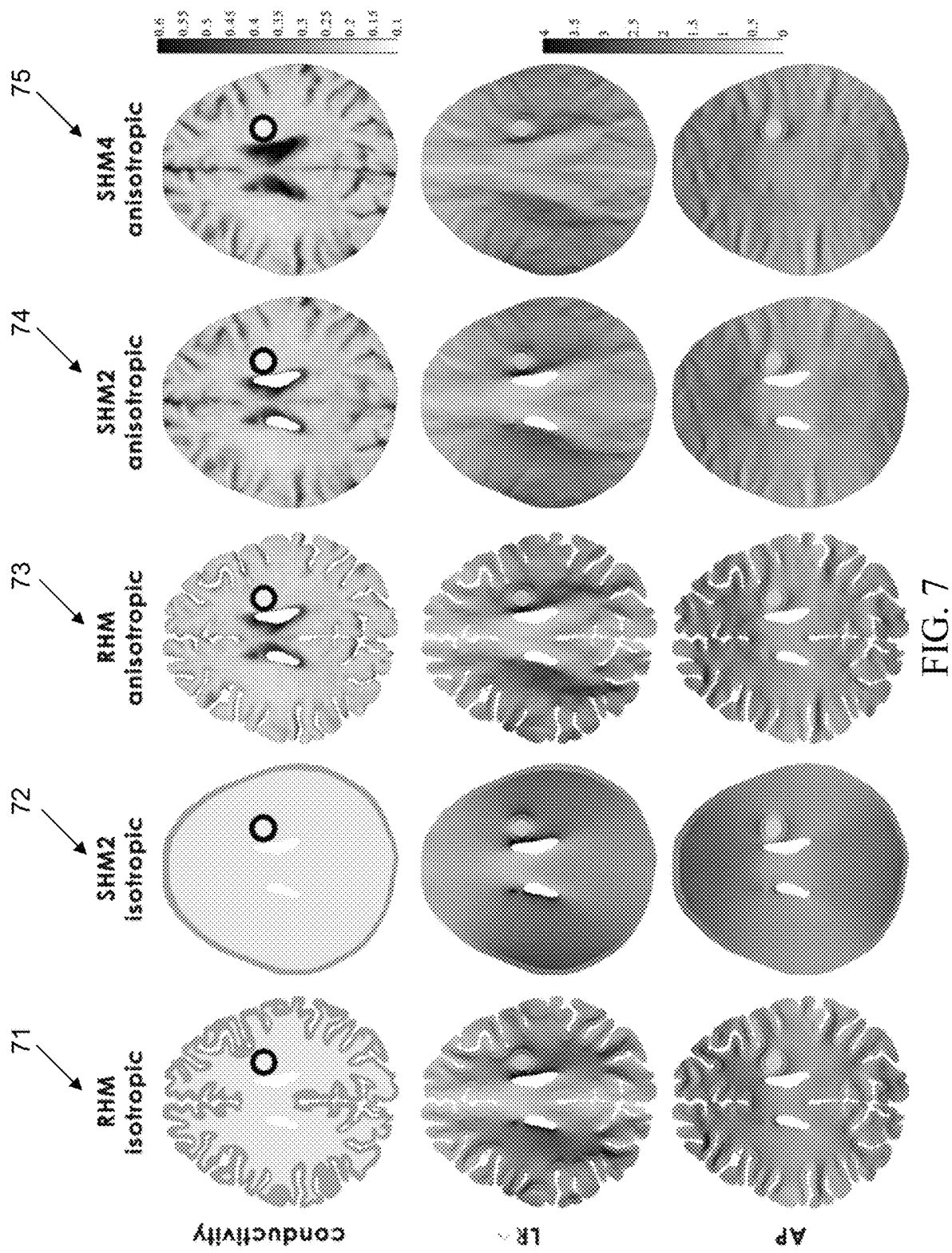
FIG. 7 depicts the conductivity map and resulting electric field distributions in the cortical and tumor tissues in an axial slice for five respective models.

FIG. 7 contains five panels 71-75, each of which depicts the conductivity map and resulting electric field distributions in the cortical and tumor tissues in an axial slice for a respective model. In each panel 71-75, the trace of the conductivity tensor appears on top, where the legend for the tensor trace is fixed and ranges from 0.1-0.6 S/m. The color of the tumor tissues is arbitrary in this figure. In each panel the electric field distribution for the LR and AP electrodes appears in the middle and bottom, respectively, and the intensity legend ranges from 0-4 V/cm.

Panels 71 and 72 illustrate the isotropic RHM and SHM2 model with their isotropic brain and tumor conductivities. Although the electric field distribution in the brain has only minor detail in SHM2 the field distribution in the tumor is similar for both LR and AP setups and the induced average field strength are similar (Table 2). When anisotropy is introduced for the brain tissues the field distribution in the brain of the RHM model is only slightly altered (compare panels 71 and 73); and the SHM2 anisotropic model (panel 74) shows increased detail and the calculated average field strength values are more coherent with those of the anisotropic RHM model (panel 73).

The SHM2 model (panel 74) was taken as baseline model for the further simplifications of SHM3 and SHM4 described above. Given the fact that the GM and WM are only represented by two convex hulls, no effect was expected from removing the inner shell, since the dM approach was used for scaling of the conductivity tensors. Indeed, almost no changes were found in the average field strength values (Table 2).

The ventricles are a complex structure in the center of the brain filled with CSF and thus are considered to be isotropic. Thus, the information estimated from DTI data is usually omitted for electric field calculations with realistic head models and a detailed segmentation with isotropic conductivities is used. SHM4 was created to investigate the effect of neglecting the segmentation of the ventricles and accounting for their presence by using the tensor evaluated from the DTI dataset. The resulting trace of the conductivity tensor is displayed in the top of panel 75. The average field strength in the brain is only slightly higher in RHM than in SHM4 (102% in LR and 101% in AP). In the tumor shell the highest field strength increase in RHM compared to the SHM4 model is 114% for LR (Table 2). This provides an indication that despite the additional simplification introduced in the SHM4 model, the results are still acceptable.

Table 2 depicts variations in field strength between the various models in both the LR and AP directions. Note that SHM3 and SHM4 in Table 2 correspond, respectively, to the Simple1 and Simple2 models in table 1 above.

TABLE 2

Average Field Strength (V/cm) in the
Brain and Tumor Tissues in Different Models

| Model | conductivity | LR brain | LR shell | AP brain | AP Shell |
|---|---|---|---|---|---|
| RHM | iso | 1.41 | 1.59 | 1.43 | 1.13 |
| SHM1 | iso | 1.93 | 1.88 | 1.98 | 1.37 |
| SHM2 | iso | 1.53 | 1.49 | 1.56 | 1.10 |
| RHM/SHM1 | | 73% | 85% | 72% | 82% |
| RHM/SHM2 | | 92% | 107% | 92% | 103% |
| RHM | aniso dM | 1.39 | 1.76 | 1.43 | 1.20 |
| SHM1 | aniso dM | 1.64 | 2.06 | 1.69 | 1.41 |
| SHM2 | aniso dM | 1.35 | 1.67 | 1.38 | 1.17 |
| SHM3 | aniso dM | 1.35 | 1.67 | 1.39 | 1.18 |
| SHM4 | aniso dM | 1.36 | 1.54 | 1.42 | 1.26 |
| RHM/SHM1 | | 85% | 85% | 84% | 85% |
| RHM/SHM2 | | 103% | 105% | 103% | 102% |
| RHM/SHM3 | | 103% | 105% | 103% | 102% |
| RHM/SHM4 | | 102% | 114% | 101% | 95% |

The presented approach can be used to rapidly create head models of patients with GBM for personalized treatment plans of TTFields. The scalp outline could be obtained by segmenting a structural image with known software in a minimum amount of time. Alternatively, head measurements could be used to predict the overall head shape. Following layers (skull, CSF, brain) could be created by thickness measurements from the structural image. Summarizing, the proposed technique should be easily applicable for future modeling, since the convex hulls outside the brain can be generated generically with the measurements of the head as only input. As for the tumor and the brain itself, a DTI dataset for the patient is used to determine the dielectric properties (e.g., conductivity).

The acquisition of DTI is not standard, however, Diffusion Weighted Imaging (DWI) with less direction is quite commonly acquired and the trace of the conductivity tensor can be estimated by only three directions. In alternative embodiments, the induced field distribution can be determined using only the trace values in each voxel and not the full tensor. This would provide an additional simplification of the model, at the possible expense of accuracy.

DTI is still a relatively new technique and image resolution is quite low (i.e., >1 mm$^3$ isotropic). As a result, careful choice of image correction and tensor estimation method is important and appropriate interpolation method is advisable. For scaling the diffusion tensor to the conductivity tensor two methods are introduced. Additionally to the dM approach, in the volume normalized (vN) method the geometric mean of the eigenvalues are matched to the isotropic reference values for each voxel. To accomplish that an underlying segmentation of the tissue type may be implemented. In some embodiments, the estimated trace of the tensor in each voxel could be used to classify the tissue type and serve as a proxy for segmentation.

As already pointed out, there already exist automated segmentation algorithms for detailed GBM segmentation. An example of a publicly available algorithm is the recent Brain Tumor Image Analysis (BraTumIA) software which distinguishes necrotic core, edema, non-enhancing tumor and enhancing tumor while needing four different imaging modalities (T1, T1-contrast, T2-contrast, and FLAIR). Techniques which only need a T1 as input also exist. Still, the heterogeneous environment of a GBM and surrounding edema might even be depicted in more detail with a voxel-wise tensor representation. Thus, although the simplified model has reduced complexity, it can still be used to describe the electric field distribution of TTFields in more detail.

This section (i.e., part 3) presents a first attempt to create simple head models which provide accurate results for calculating the electric field distribution for the application of TTFields. The electric field strength in one central tumor did not change significantly when using a simple model compared to a realistic human head model derived from structural images. The method described herein can be extended to create personalized models without the need for time-consuming tissue segmentation. In future, this method could be used to rapidly develop individual patient head models with a detailed representation of their lesion, albeit with the requirement that a DTI dataset is available.

Once the layout that optimizes the electric field within the diseased regions of the patient's brain has been determined (e.g., using any of the approaches explained herein), the electrodes are positioned in the determined positions. AC voltages are then applied to the electrodes (e.g., as described in U.S. Pat. No. 7,565,205, which is incorporated herein by reference) to treat the disease.

Note that the concepts described herein are not limited to using DTI to derive the electric properties of the brain. To the contrary—it extends to other methods that can be used for the same purpose including but not limited to DWI, Electric Conductivity Imaging, Electric Impedance Tomography (EIT) and multi echo GRE.

Note also that the concepts described herein are not limited to representations of the outer layers (scalp, skull, CSF) as convex hulls, and other methods may be used to roughly approximate the MRI data. Examples include simple geometric forms such as ellipsoids, spheres, oval shaped structure or also other methods for creating an envelope of the tissues. Additionally, the concepts described herein are not restricted to an approximation of the outer layers, i.e., the scalp, skull and CSF layers can also be obtained through conventional segmentation of MRIs.

Optionally, post-processing of conductivity maps to improve results (e.g.: smoothing or outlier removal/replacement, adapted interpolation techniques, etc.) may be implemented. Furthermore, other mapping methods from diffusion to conductivity methods may be used, as well as a combination of the two mentioned methods (e.g., the dM and vN approach). Thus, it may be advantageous to use the dM for the cortical tissues, and the vN for the ventricles and the tumor tissues including an edema region which all might have been identified as regions of interest (ROIs) by a clinician or radiologist.

Some of the embodiments described above use a mixed method in which some volume elements are assigned representative electric properties of the tissue types they belong to, whereas others are assigned electric properties based on the specific MRI sequence data (in this case DTI). For example, the skull, scalp and CSF were assigned representative isotropic dielectric properties, whereas the conductivities of the white and grey matter (and ventricles in some embodiments) were derived from the DTI data. Note that in the presented case also the tumor tissues were assigned isotropic dielectric properties at a virtual location, since the images originated from a healthy subject. In alternative embodiments, however, total amount of volume elements within the whole head may be assigned either isotropic or anisotropic dielectric properties that were solely derived from a specific imaging technique.

Note that in some embodiments, only the boundary surface of the head is identified, e.g., by conventional segmentation of the scalp surface, and conductivity and/or permittivity are assigned to all points within the phantom using the conductivity measurements derived from the MIll conductivity measurements.

In some embodiments, the brain is identified using existing whole brain extraction algorithms. Next, the scalp, skull, and CSF are segmented using an automatic procedure. Conductivity values are assigned to the brain, the tumor tissues (including active shell and necrotic core), a possible edematous region, and the ventricles using the Mill conductivity measurements. Bulk conductivity values are assigned to the scalp, skull, and CSF.

In some embodiments, the brain is identified using existing whole brain extraction algorithms. Next, the scalp, skull, CSF, and ventricles are segmented using an automatic procedure. Conductivity values are assigned to the brain, the tumor tissues (including active shell and necrotic core), and a possible edematous region using the MM conductivity measurements. Bulk conductivity values are assigned to the scalp, skull, CSF, and ventricles.

In some embodiments, the brain is identified using existing whole brain extraction algorithms. The tumor is marked as a ROI by a clinician or radiologist. Next, the scalp, skull and CSF are segmented using an automatic procedure. Conductivity values are assigned to the brain and the ventricles using the MM conductivity measurements. Bulk conductivity values are assigned to the scalp, skull, CSF, and the tumor tissues (e.g., by assigning a constant conductivity value to each of those regions).

Note also that instead of using the segmentation of the scalp, skull, and CSF, an approximation of these outer layers may be used. For example, the user may be asked to measure the thickness of the scalp, skull, and CSF in a representative region. These tissues are then approximated as concentric geometric entities (similar to a default convex hull of a scalp, a sphere, an ellipsoid, etc.) with the user-measured thicknesses surrounding the brain. This approximation simulates the head as an (almost) oval shaped structure, ignoring features such as the ears, nose, mouth and jaw. However, since the arrays and treatment are delivered only to the supratentorial region of the head, this approximation appears to be justified. In some embodiments it might also be possible to combine two or more of the three tissue types into one layer and assign a single conductivity value to that layer. For instance, the scalp and skull may be introduced as one layer with a single conductivity (and optionally a uniform thickness).

The inventors expect that the ability to develop realistic head models for individual patients will not only allow for optimization of the electric field within the tumor, but may also enable treatment planning that mitigates out-of-field reoccurrences. This could be achieved by developing optimization methods that not only account for the electric field intensity within the tumor, but also try to optimize the field intensity in other regions of the brain.

Optionally, patient-specific computational head models may be used for retrospective patient analysis that could clarify the connection between field strength distributions and disease progression within patients, ultimately leading to a better understanding on how to deliver TTFields in patients.

Computational phantoms built in this manner could also be used for other applications in which calculating electric field and or electric current distributions within the head may be useful. These applications include, but are not limited to: direct and alternating current trans-cranial stimulation; simulations of implanted stimulatory electrode field maps; planning placement of implanted stimulatory electrodes; and source localization in EEG.

Finally, although this application describes a method for optimizing array layouts on the head, it could potentially be extended for optimizing array layouts for treatment of other body regions such as the thorax or abdomen.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method of optimizing positions of a plurality of electrodes placed on a subject's body, wherein the electrodes are used to impose an electric field in target tissue within an anatomic volume, the method comprising the steps of:
    generating a 3D map of electrical conductivity or resistivity of the anatomic volume;
    identifying a location of the target tissue within the anatomic volume;
    adding a dipole to the 3D map at a location that corresponds to the target tissue; and
    determining positions for the electrodes that maximize a potential attributable to the dipole based on the 3D map of electrical conductivity or resistivity generated in the generating step and the location of the dipole.

2. The method of claim 1, wherein the location at which the dipole is added corresponds to a center of the target tissue.

3. The method of claim 2, wherein the added dipole is aligned with a direction of an expected electric field.

4. The method of claim 3, further comprising the steps of:
    affixing the electrodes to the subject's body at the positions determined in the determining step; and
    applying electrical signals between the electrodes subsequent to the affixing step, so as to impose the electric field in the target tissue.

5. The method of claim 1, further comprising the steps of:
    affixing the electrodes to the subject's body at the positions determined in the determining step; and
    applying electrical signals between the electrodes subsequent to the affixing step, so as to impose the electric field in the target tissue.

6. The method of claim 1, further comprising obtaining electrical conductivity or resistivity measurements in the anatomic volume,
    wherein the 3D map of electrical conductivity or resistivity of the anatomic volume is generated directly from the obtained electrical conductivity or resistivity measurements, without segmenting the anatomic volume into tissue types.

7. The method of claim 6, wherein the obtaining comprises acquiring MRI data using diffusion weighted imaging.

8. The method of claim 6, wherein the obtaining comprises acquiring MRI data using customized multi echo gradient sequences.

9. The method of claim 6, wherein the obtaining comprises acquiring MRI data using diffusion tensor imaging.

* * * * *